(12) United States Patent
Schuler et al.

(10) Patent No.: US 7,814,905 B2
(45) Date of Patent: *Oct. 19, 2010

(54) SYSTEMS DEVICES AND METHODS FOR OPENING RECEPTACLES HAVING A POWDER TO BE FLUIDIZED

(75) Inventors: Carlos Schuler, Cupertino, CA (US); William A. Alston, San Jose, CA (US); Derrick Tuttle, San Jose, CA (US); Dennis Rasmussen, Santa Clara, CA (US); Stephen R. Demming, San Jose, CA (US)

(73) Assignee: Novartis AG, Basel (CH)

( * ) Notice: Subject to any disclaimer, the term of this patent is extended or adjusted under 35 U.S.C. 154(b) by 790 days.

This patent is subject to a terminal disclaimer.

(21) Appl. No.: 10/675,602

(22) Filed: Sep. 29, 2003

(65) Prior Publication Data

US 2005/0161041 A1    Jul. 28, 2005

Related U.S. Application Data

(63) Continuation of application No. 09/853,173, filed on May 9, 2001, now Pat. No. 6,668,827.

(60) Provisional application No. 60/204,526, filed on May 16, 2000.

(51) Int. Cl.
*A61M 16/00* (2006.01)
*A61M 15/00* (2006.01)
*B27B 5/12* (2006.01)
*B23B 51/00* (2006.01)
*B26B 19/14* (2006.01)

(52) U.S. Cl. .............. 128/203.15; 128/203.21; 408/204; 408/207; 408/227; 408/230; 30/43.4; 30/43.5; 30/43.6

(58) Field of Classification Search .......... 128/203.21, 128/203.15; 408/204, 227, 207, 230; 30/43.4, 30/43.5, 43.6
See application file for complete search history.

(56) References Cited

U.S. PATENT DOCUMENTS

| 2,566,653 | A | 9/1951 | Gripp et al. |
| 3,624,681 | A | 11/1971 | Zuurveen et al. |
| 3,874,078 | A | 4/1975 | Raque |
| 3,962,784 | A | 6/1976 | Tietjens |
| 4,475,285 | A | 10/1984 | Hara et al. |

(Continued)

FOREIGN PATENT DOCUMENTS

EP        0568036        11/1993

(Continued)

*Primary Examiner*—Patricia M Bianco
*Assistant Examiner*—Nihir Patel
(74) *Attorney, Agent, or Firm*—Janah & Associates, P.C.

(57) ABSTRACT

A method for forming at least one opening in a receptacle comprises the steps of providing a receptacle having a cover with an exterior surface and an interior surface covering a cavity. A cutting mechanism is also provided having at least one blade. The cover is pierced with the blade, and the blade is moved through the cover to cut a portion of the cover and create an opening in the cover to provide access into the cavity. Further, the cut portion curls on top of the exterior surface as the opening is created.

30 Claims, 7 Drawing Sheets

U.S. PATENT DOCUMENTS

| | | |
|---|---|---|
| 4,521,965 A | 6/1985 | Walker |
| 4,628,584 A | 12/1986 | Clark et al. |
| 4,707,923 A | 11/1987 | Tietjens |
| 4,729,169 A | 3/1988 | Asawa |
| 4,778,054 A * | 10/1988 | Newell et al. ............... 206/531 |
| 5,207,217 A | 5/1993 | Cocozza et al. |
| 5,390,416 A | 2/1995 | Uchiyama et al. |
| 5,415,162 A | 5/1995 | Casper et al. |
| 5,458,135 A | 10/1995 | Patton et al. |
| 5,654,007 A | 8/1997 | Johnson et al. |
| 5,740,794 A * | 4/1998 | Smith et al. ............ 128/203.15 |
| 5,775,320 A | 7/1998 | Patton et al. |
| 5,780,014 A | 7/1998 | Eljamal et al. |
| 5,785,049 A | 7/1998 | Smith et al. |
| 5,816,404 A * | 10/1998 | Seidler ....................... 206/461 |
| 5,922,354 A | 7/1999 | Johnson et al. |
| 5,993,783 A | 11/1999 | Eljamal et al. |
| 6,033,159 A | 3/2000 | Kress et al. |
| 6,089,228 A | 7/2000 | Smith et al. |
| 6,103,270 A | 8/2000 | Johnson et al. |
| 6,257,233 B1 | 7/2001 | Burr et al. |
| 6,470,884 B2 | 10/2002 | Horlin |
| 6,543,448 B1 | 4/2003 | Smith et al. |
| 6,546,929 B2 | 4/2003 | Burr et al. |
| 6,606,992 B1 | 8/2003 | Schuler et al. |
| 6,668,827 B2 * | 12/2003 | Schuler et al. ......... 128/203.21 |
| 6,679,256 B2 | 1/2004 | Ingle et al. |
| 2003/0136400 A1 | 7/2003 | Klimowicz et al. |
| 2004/0139968 A1 | 7/2004 | Loeffler et al. |

FOREIGN PATENT DOCUMENTS

| | | |
|---|---|---|
| JP | 08164995 | 6/1996 |
| JP | 08276990 | 10/1996 |
| WO | WO 97/40876 | 11/1997 |
| WO | WO 99/32180 | 7/1999 |
| WO | WO 99/47099 | 9/1999 |
| WO | WO 00/72904 | 12/2000 |
| WO | WO 01/00263 | 1/2001 |
| WO | WO 01/43529 | 6/2001 |

* cited by examiner

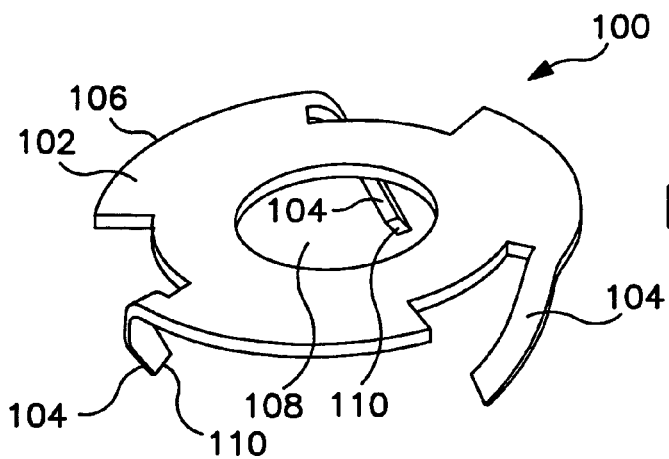
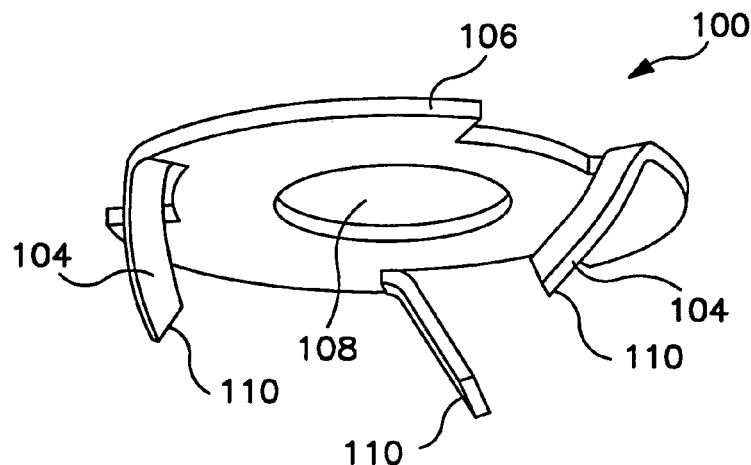
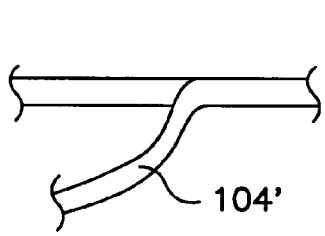
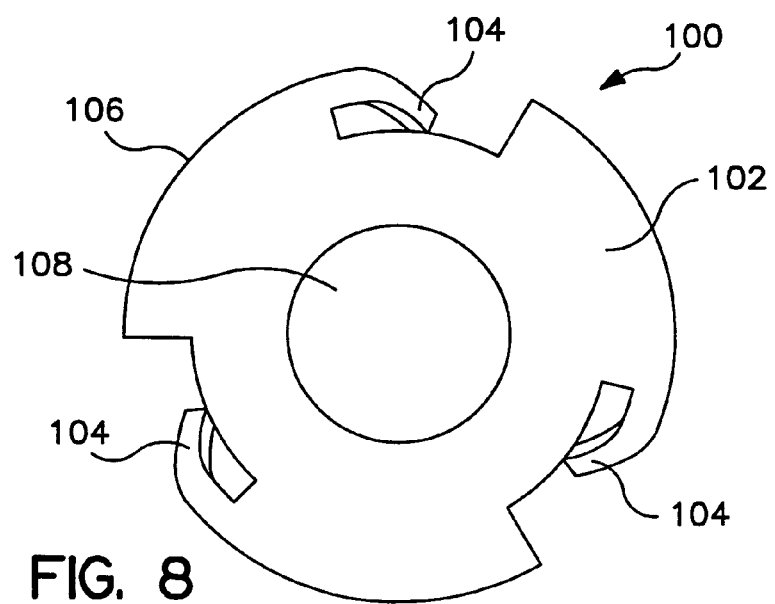

SYSTEMS DEVICES AND METHODS FOR OPENING RECEPTACLES HAVING A POWDER TO BE FLUIDIZED

BACKGROUND OF THE INVENTION

This invention relates generally to the field of drug delivery, and in particular to the pulmonary delivery of powdered medicaments. More specifically, the invention relates to techniques for forming openings in receptacles to facilitate extraction of powdered medicaments from the receptacles during the aerosolizing process.

One promising way to deliver various drugs to a patient is by pulmonary delivery where a drug dispersion or aerosol is inhaled by the patient to permit the active drug within the dispersion to reach the distal or alveolar regions of the lung. Pulmonary drug delivery has shown to be particularly promising because certain drugs have been found to readily absorb within the blood circulation. For example, pulmonary delivery may be a useful approach for proteins and polypeptides that are difficult to deliver by other routes of administration.

A variety of techniques have been employed to deliver drugs to the lungs including liquid nebulizers, metered dose inhalers, and the like. Of particular interest to the invention are dry powder dispersion devices that are able to aerosolize powdered medicaments for inhalation by the patient. Exemplary apparatus for aerosolizing powdered medicaments are described in U.S. Pat. Nos. 5,458,135, 5,775,320, 5,740,794 and 5,785,049, and copending U.S. patent application Ser. No. 09/004,558, filed Jan. 8, 1998, Ser. No. 09/312,434, filed Jun. 4, 1999, 60/136,518, filed May 28, 1999, and 60/141,793, filed Jun. 30, 1999, the complete disclosures of which are herein incorporated by reference.

At least some of the apparatus described in the above references utilize a gas stream to draw the powder into an extraction tube where the powder is deagglomerated, entrained in the gas stream, and exits as an aerosol suitable for inhalation. In some cases, such apparatus may utilize a receptacle that has a penetrable lid. The extraction tube is inserted through the lid and a vent is also formed in the lid. The gas stream then draws air through the receptacle and into the extraction tube. The air drawn through the receptacle extracts the powder where it joins with the gas stream to form the aerosol. It is also possible to extract the powder from within a receptacle by use of a breath actuated device as described in U.S. Patent Application Ser. No. 60/141,793 cited above.

Hence, when utilizing such receptacles to hold the powder, a need exists for creating inlet and outlet openings in the receptacles to facilitate extraction of the powder. The manner in which these openings are created can be challenging. For example, it may be convenient to form such openings while the receptacle is within the aerosolizing apparatus. Due to the relatively small size of such apparatus, the proper formation of appropriately configured holes presents many technical challenges.

Further, in some cases, the openings may need to be precisely located and have a specified size. This can be especially challenging because of the wide variety of cavity shapes. Merely by way of example, copending U.S. Patent Application Ser. No. 60/172,317, filed Dec. 17, 1999, the complete disclosure of which is herein incorporated by reference, describes several shapes of cavities that may be used to hold a powder. Another challenging aspect may be the need to minimize the amount of material that is forced into the cavity during formation of the openings in order to increase the gas flow efficiency through the cavity.

Hence, the invention is related to techniques for forming openings in receptacles to maximize the efficiency with which the powder may be extracted and aerosolized.

SUMMARY OF THE INVENTION

In one embodiment, a method is provided for forming at least one opening in a receptacle that includes a cover with an exterior surface and an interior surface that covers a cavity. The cover is pierced with a blade of a cutting mechanism. The blade is then moved through the cover to cut a portion of the cover and create an opening in the cover to provide access into the cavity. As the blade is moved through the cover, the cut portion curls on top of the exterior surface so as to be outside of the cavity.

In one aspect, the cutting mechanism is rotated after the cover has been pierced to move the blade through the cover. Such a feature is advantageous in that a curved opening may be created in the cover. In another aspect, the cutting mechanism includes multiple blades so that multiple openings may be formed simultaneously when the cutting mechanism is rotated. In one specific aspect, the cutting mechanism may include three blades, and the cutting mechanism is rotated through an angle in the range from about 70 degrees to about 115 degrees to form three curved elongate openings in the cover. However, it will be appreciated that other numbers of blades may also be used.

In another particular aspect, the cutting mechanism comprises a support member, with the blade being angled in a forward direction relative to the support member by an angle in the range from about 50 degrees to about 80 degrees and more preferably from about 60 degrees to about 70 degrees. The blade is moved through the cover in the forward direction to permit the blade to direct the cut portion of the cover onto the exterior surface and away from the cavity. As the cut portion is removed, it rolls into a ball in one "in tact" piece that remains attached to the cover. In another particular aspect, the cavity has an outer periphery, and the opening is formed near or along the outer periphery. For example, at least a portion of the outer periphery may be curved. As the cutting mechanism is rotated, the opening that is produced is also curved and follows along the outer periphery.

In still another aspect, a central opening is formed in the cover while forming the elongate opening. Conveniently, a center cutting device may be employed to form the central opening while the elongate opening is also being formed. In this way, the cutting mechanism may be employed to simultaneously create inlet openings and an outlet opening to facilitate extraction of a powder from the cavity. Conveniently, the center cutting device may comprise a tubular member that extends from the support member. To form the central opening, the cover may be pierced with the blades of the center cutting device. The support member may then be rotated to form the central opening. One particular advantage of using the tubular member is that it may be used as a flow path when extracting the powder from the cavity. In one aspect, the outlet opening is formed first, followed by the outlet openings.

In another embodiment, a method is provided for aerosolizing a powder that is contained within a receptacle having a cover with an exterior surface and an interior surface covering a cavity that contains the powder. The method utilizes a cutting mechanism having at least one outer blade and a plurality of inner blades. According to the method, the cover is pierced with the outer blade and the inner blades, and the outer blade is moved through the cover to cut a portion of the cover and to create an elongate outer opening in the cover. As the outer opening is created, the cut portion curls on top of the exterior surface. Simultaneously, the inner blades are moved through the cover to cut an inner opening in the cover. Air is then drawn through the outer opening, through the cavity and out the inner opening to extract the powder from the receptacle and to aerosolize the powder.

In one particular aspect, the cutting mechanism comprises a support member from which the outer blade extends. The support member is maintained at a location that is spaced above the cover when cutting the openings and when extracting the powder. Such a configuration is convenient when the receptacle is opened within an aerosolizing apparatus where space may be limited. In one particular aspect, the outer opening has a width, B, and the support member is maintained at a location spaced apart from the cover by a distance, A, where A is greater than or equal to B. In still another aspect, the width, B, is in the range from about 0.3 mm to about 2 mm.

In still another aspect, a tubular member extends from the support member, with the inner blades being formed on the tubular member. As the support member is rotated, the inner blades on the tubular member form the inner opening. Conveniently, a gas stream may be flowed through at least a portion of the tubular member to draw the air through the cavity and out the tubular member. In this way, the same tubular member that is employed to form the inner opening may also be used in extracting the powder from the receptacle using a flowing gas stream.

In still another embodiment, a hole forming device is provided which comprises a support member and a plurality of outer blades extending downward from the support member at an angle in the range from about 50 degrees to about 80 degrees and more preferably from about 60 degrees to about 70 degrees. A tubular member extends downward from the support member, with the tubular member being surrounded by the outer blades. A distal end of the tubular member includes a plurality of inwardly directed and outwardly facing blades. With such a configuration, the hole forming device may be employed to form a plurality of outer openings and an inner opening as the blades are pierced through a cover and then rotated through the cover.

In one embodiment, an aerosolizing apparatus is provided which comprises a housing for holding a receptacle having a cover with an exterior surface and an interior surface covering a cavity that contains a powder. Disposed in the housing is a hole forming device for forming at least one inlet opening and an outlet opening in the cover. An aerosolizing system is also provided to extract powder from the receptacle by drawing air through the inlet opening, through the receptacle and out the outlet opening. The hole forming device comprises a support member having at least one outer blade that extends downward from the support member at an angle in the range from about 50 degrees to about 80 degrees and more preferably from about 60 degrees to about 70 degrees. The hole forming device also includes at least one inner blade. A moving mechanism is further provided to move the support member relative to the receptacle to move the outer blade through the cover and cause a cut portion of the cover to curl on top of the exterior surface to form the inlet opening, and to cut an outlet opening with the inner blade. Hence, with the aerosolizing apparatus, a receptacle may be placed into the housing and the hole forming device utilized to form an inlet opening and an outlet opening. The aerosolizing system may then be employed to extract the powder from the receptacle where it will be available for inhalation by a patient.

Conveniently, the hole forming device may include a plurality of outer blades for forming multiple inlet openings. Further, the hole forming device may include a tubular member that extends downward from the support member, with the distal end of the tubular member including a plurality of inwardly directed and outwardly facing inner blades. In this way, a gas stream may be flowed through at least a portion of the tubular member to draw gases through the inlet openings, through the cavity and through the tubular member to extract and aerosolize the powder. Conveniently, the gas stream may be produced by a gas source that is disposed within the housing. Alternatively, the aerosolizing apparatus may include a mouthpiece so that as the patient inhales from the mouthpiece, a gas stream is caused to flow through at least a portion of the tubular member to extract the powder.

BRIEF DESCRIPTION OF THE DRAWINGS

FIG. 6 is a top perspective view of a cutting mechanism according to the invention.

FIG. 7 is a bottom perspective view of the cutting mechanism of FIG. 6.

FIG. 8 is a top plan view of the cutting mechanism of FIG. 6.

FIG. 8A is a side view of an alternative cutting mechanism.

DESCRIPTION OF THE SPECIFIC EMBODIMENTS

Figure 1:
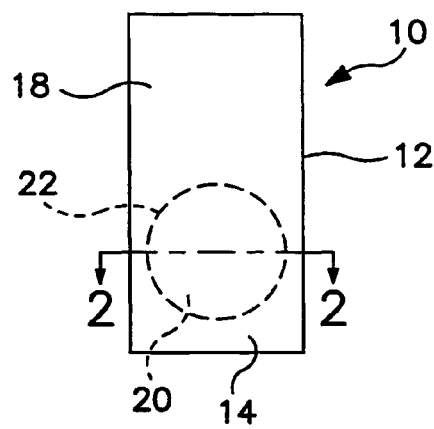
FIG. 1 is a top view of one embodiment of a receptacle for holding a powder according to the invention.

The invention provides exemplary techniques and equipment for forming openings in receptacles having a sealed cavity in which a powder is held. In this way, a gas stream may be permitted to flow through the cavity to extract and aerosolize the powder so that it will be suitable for inhalation by a patient. The invention may be utilized with essentially any type of receptacle within which the powder is sealed. Merely by way of example, one type of receptacle that may be utilized with the invention are widely available "blister packs". Examples of other types of receptacles are described in U.S. Pat. No. 5,740,794 and in U.S. Patent Application Ser. No. 60/172,317, filed Dec. 17, 1999, previously incorporated by reference. However, it will be appreciated that the invention is not intended to be limited to these specific types of receptacles.

The powders of the invention may be extracted by creating an opening or access way into the receptacle and then flowing air or other gases through the receptacle to move the powder out of the access way. One or more vents may also be created in the receptacle to facilitate the flow of air through the receptacle. One exemplary way to draw air through the receptacle is by use of an extraction tube that is inserted into the cavity. A gas stream is flowed through at least a portion of the extraction tube to cause air in the receptacle to be drawn into the bottom end of the extraction tube where the powder is entrained in the gas stream to form an aerosol. Examples of techniques that employ the use of such an extraction tube are described in U.S. Pat. No. 5,740,794, previously incorporated by reference. Further, a variety of techniques may be employed to create the gas stream to cause the air to be drawn through the receptacle. For example, various techniques for producing the gas stream are described in U.S. Pat. No. 5,740, 794 and copending U.S. patent application Ser. Nos. 09/004, 558, 09/312,434, 60/136,518, 60/141,793, and 60/172,317, previously incorporated herein by reference. Gases that may be used to produce the gas stream include air, $CO_2$, HFCs, CFCs, and the like.

To draw air through the receptacle and into the bottom end of the extraction tube, the gas stream may be introduced into the extraction tube at a location that is spaced apart from the bottom end. For example, the gas stream may be introduced into the extraction tube at an acute angle as described generally in U.S. Pat. No. 5,740,794, previously incorporated by reference. Alternatively, a hole may be formed in the bottom end of the receptacle, and the extraction tube inserted into the top end of the receptacle so that it is generally aligned with the hole. The gas stream may then be flowed through the hole and into the extraction tube to cause air to be drawn through the receptacle and into the bottom end of the extraction tube as described in U.S. Patent Application Ser. No. 60/172,317, previously incorporated by reference.

Alternatively, the invention may utilize a patient's own inhalation to produce a gas stream. For example, the invention may utilize a mouthpiece over which the patient's mouth is placed. As the patient inhales, a vacuum is created to produce a gas stream that flows through the receptacle as described above.

The invention may utilize a variety of techniques, alone or in combination, to form one or more inlet openings and one or more outlet openings in the receptacles to facilitate extraction of the powder. The number of openings, their size, their location in the receptacle, their geometry, and their manner of formation may depend upon a variety of factors. Such factors may include, for example, the design of the aerosolizing apparatus, the design of the receptacle, the type of powder, and the like. For example, a variety of schemes may be employed, alone or in combination, to facilitate the extraction of the powder using air flowing through the receptacle. For instance, one technique employs the use of air or other gases to uniformly "scrub" the sides of the cavity. Another technique to facilitate removal of the powder is to accelerate the flow of air through the receptacle. One convenient way to accelerate the air flow is to progressively decrease the area through which the air passes as it flows through the receptacle and out of the extraction tube. By progressively reducing the flow area, the air is accelerated as it flows through the receptacle and into the extraction tube. Such techniques are described generally in U.S. Patent Application Ser. No. 60/172,317, previously incorporated by reference. Depending on the particular scheme, the receptacle may have different cavity configurations, or may need to incorporate specifically designed openings.

For instance, the cavity may have curved walls to facilitate scrubbing, thereby creating a curved outer perimeter. Hence, with some embodiments, curved inlet openings are formed at the outer perimeter. In some cases, the inlet and outlets may need to be a certain size to facilitate acceleration of the gases through the cavity as just described. Hence, in one aspect, the openings are formed to be within appropriate size ranges.

As another example, the holes in the receptacle may be configured to be offset from a set of openings in a tool used to create the holes. The offset arrangement of the receptacle holes and the openings of the tool causes air to tangentially enter through the holes of the receptacle and into the cavity. With such a configuration, a vortex may be created within the cavity to scrub the receptacle walls as the powder is extracted.

In another aspect, one or more of the openings may be formed while the receptacle is in the aerosolizing apparatus. In this way, the user may simply insert a receptacle into the apparatus and then operate the apparatus to form the openings and aerosolize the powder. Alternatively, stand alone hole forming devices may be used to create the openings prior to insertion into an aerosolizing device.

The openings may be formed in the receptacle by using one or more blades to make a cut or an incision in the material forming top surface of the receptacle, i.e. the cover of the receptacle. The blade is then moved through the cover an appropriate distance. As the blade moves through the cover, the cut portion of the cover is directed outwardly from the cavity. In this way, the cavity remains free of any tabs or burrs created when forming the openings so that gases may flow unhindered through the cavity. The blades may also be configured to prevent any cut material from falling into the cavity so that this will not be inhaled by the patient. Further, the blades may be configured to form the openings without crushing or collapsing the cover.

As previously described, a wide variety of receptacles may be used with the invention. For convenience of illustration, a limited number of receptacles types will be described below to demonstrate the cutting techniques of the invention. However, it will be appreciated that the invention is not intended to be limited to only those specific receptacles.

Figure 2:
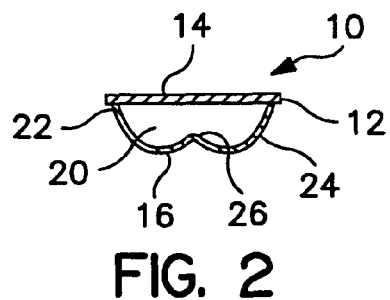
FIG. 2 is a cross sectional side view of the receptacle of FIG. 1 taken along lines 2-2.

FIGS. 1 and 2 illustrate one embodiment of a receptacle 10 containing a powder which is to be extracted after forming appropriate openings as described hereinafter. Receptacle 10 comprises a receptacle body 12 having a top end or cover 14 and a bottom end 16 (see FIG. 2). Conveniently, a tab 18 may be provided to facilitate handling of receptacle 10. Receptacle body 12 defines a cavity 20 into which the powder is sealed. Conveniently, receptacle body 12 may be constructed from essentially any type of material that is compatible with the powder held within cavity 20. Examples of materials that may be used include metals, such as aluminum, composites, plastics, and the like. One convenient way to construct receptacle 10 is to provide a thin strip of metal or composite and then pressing cavity 20 using a die. Another thin strip of metal may then be attached to the strip having the cavity to enclose and seal the cavity. Conveniently, ultrasonic welding or heat sealings may be employed to adhere the two metal strips together. However, it will be appreciated that other techniques and materials may be employed to construct receptacle 10.

Cavity 20 has a generally circular outer periphery 22 and is formed of a continuously curved wall 24 that forms a raised central region 26 at or near a center of the receptacle. In this way, a generally semi-toroidal interior is formed to facilitate removal of powder from the receptacle.

Figure 3:
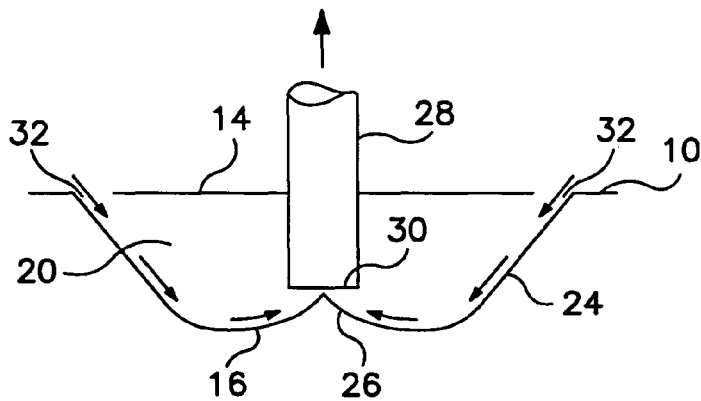
FIG. 3 schematically illustrates one technique for extracting powder from a receptacle according to the invention.

Referring now to FIG. 3, one technique for extracting powder from receptacle 10 using an extraction tube 28 will be described. A gas stream is flowed past a portion of extraction tube 28 at a location spaced above a bottom end 30 as described generally in U.S. Pat. No. 5,740,794, previously incorporated by reference. This causes air to be drawn into receptacle 10 through vents or inlet openings 32 as illustrated by the arrows. The air is flowed through cavity 20 until entering bottom end 30 where it proceeds through extraction tube 28. Eventually, the air containing the powder is joined with the gas stream that deagglomerates the powder and entrains the powder in the gas stream to form an aerosol.

Figure 4:
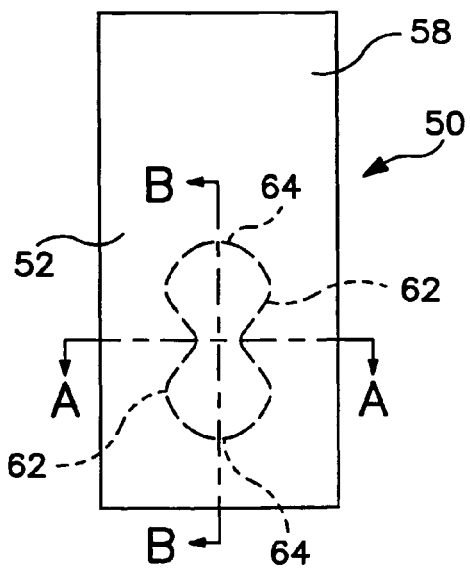
FIG. 4 is a top view of an alternative embodiment of a receptacle according to the invention.
Figure 5A:
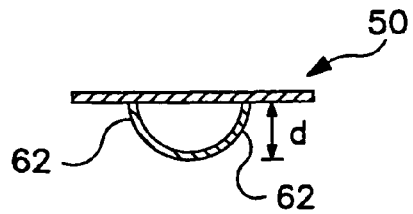
FIG. 5A is a cross sectional side view of the receptacle of FIG. 4 taken along lines A-A.
Figure 5B:
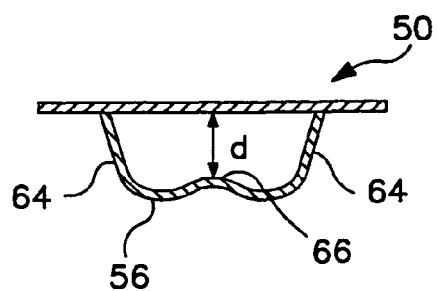
FIG. 5B is a cross sectional side view of the receptacle of FIG. 4 taken along lines B-B.

FIGS. 4, 5A and 5B illustrate another embodiment of a receptacle 50. Receptacle 50 comprises a receptacle body 52 having a top end 54, a bottom end 56 and a tab 58. Receptacle body 52 defines a cavity 60 into which a powder is held. Cavity 60 is defined by two side walls 62 and two end walls 64 to form a "bow tie" configuration. A raised central region 66 extends up into cavity 60 in a manner similar to raised central region 26 of receptacle 10.

To extract powder from receptacle 50, an extraction tube (not shown) may be inserted through top end 54 and aligned above raised central region 66 in a manner similar to that previously described in connection with receptacle 10. Vents or inlet openings may then be formed in top end 54 adjacent curved walls 64. In this manner, air will be drawn through the vents and along curved wall 64 where the air will be funneled by raised central region 66 into the bottom end of the extraction tube.

Hence, to extract the powder from the above described receptacles, a centrally located outlet opening is formed for receiving an extraction tube, and one or more inlet openings or vents are formed to permit gases to be drawn into the cavity. The invention provides various cutting tools or mechanisms to form such openings. Such cutting mechanisms may be configured to separately form the inlet openings and the outlet openings, or may incorporate blades that simultaneously form both the inlet openings and the outlet openings.

One embodiment of a cutting mechanism 100 for forming inlet openings is illustrated in FIG. 6. Cutting mechanism 100 comprises a support member 102 having a plurality of downwardly extending blades 104 at an outer periphery 106. Optionally, support member 102 may include a central opening 108 to permit support member 102 to be coupled to a tubular member as described hereinafter.

Although shown with three blades, it will be appreciated that support member 102 may be included with other numbers of blades, such as a single blade, a pair of blades, four blades, and the like depending on the number of openings that are to be formed. Blades 104 include a sharpened edge 110 to permit blades 104 to pierce a cover of a receptacle as described hereinafter. Blades 104 extend downward from support member 102 at an angle in the range from about 50 degrees to about 80 degrees, preferably from about 60 degrees to about 70 degrees, and more preferably at about 65 degrees. Such an angle facilitates outward curling of the cut portions of the receptacle cover as support member 102 is rotated while keeping the displaced foil in tact in the shape of a ball.

Blades 104 may be constructed to have a width that is approximately the same as the desired width of the openings formed in the receptacle cover. Merely by way of example, for receptacles having a cavity volume in the range from about 0.04 cc to about 0.16 cc, blades 104 may each have a width that is in the range from about 0.3 mm to about 2 mm. However, it will be appreciated that the invention is not intended to be limited to this specific size range. In one specific aspect, blades 104 may have a width that is selected to produce openings of a certain size to facilitate the acceleration of air flow through the receptacle as described generally in co-pending U.S. Application Ser. No. 60/172,317, previously incorporated by reference. Further, support member 102 may be rotated through an angle in the range from about 70 degrees to about 115 degrees, and more preferably from about 90 degrees to about 100 degrees (when three blades are employed) to form the three openings of an appropriate size. It will further be appreciated that blades 104 do not need to be straight in geometry and may take on other shapes, such as curved blades. One such example of a blade 104 is shown in FIG. 8A. Moreover, in some cases, the widths and/or angles and/or shapes may vary from blade to blade.

Figure 15:
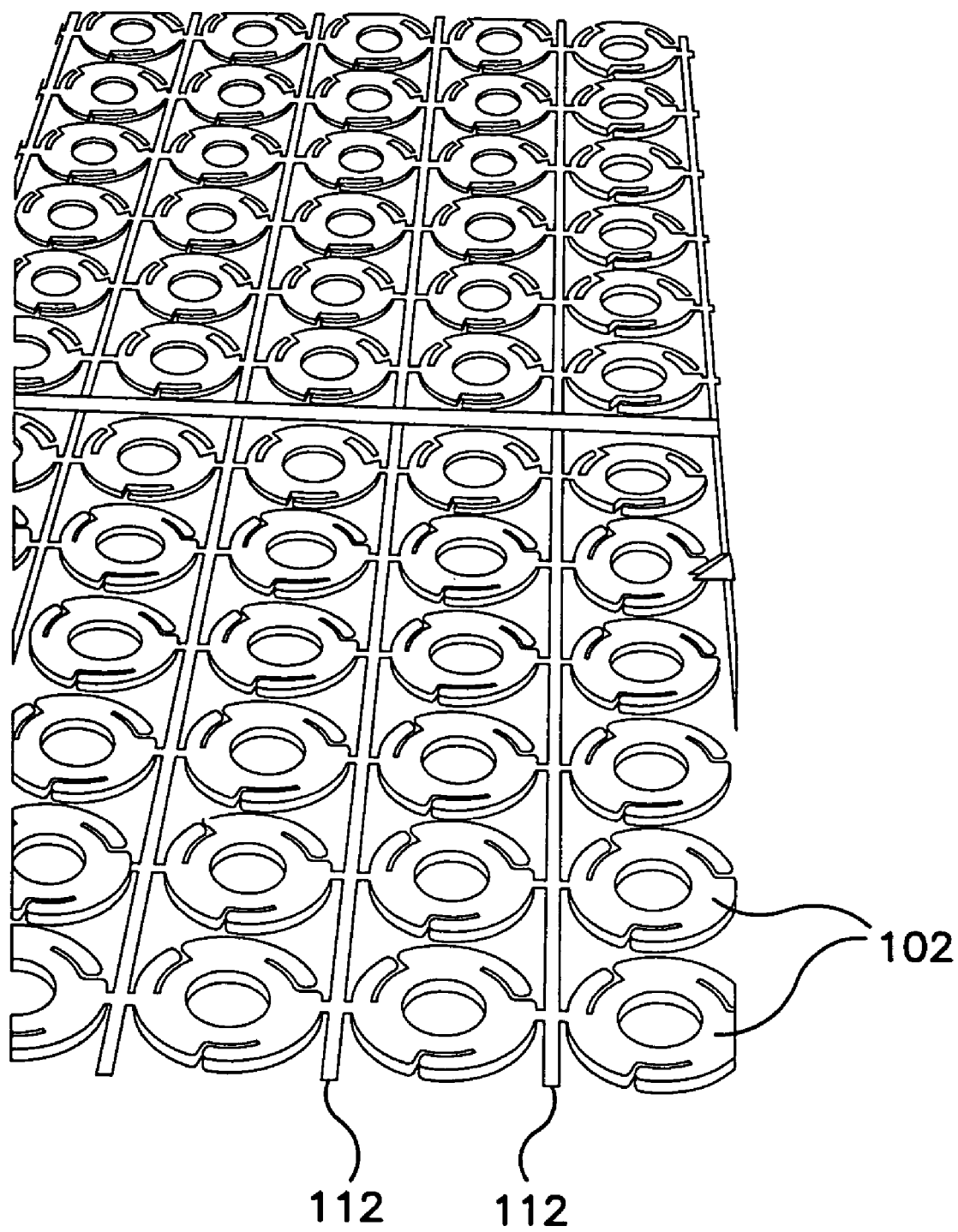
FIG. 15 illustrates a set of washers employed to form a set of cutting mechanisms according to the invention.
Figure 16:
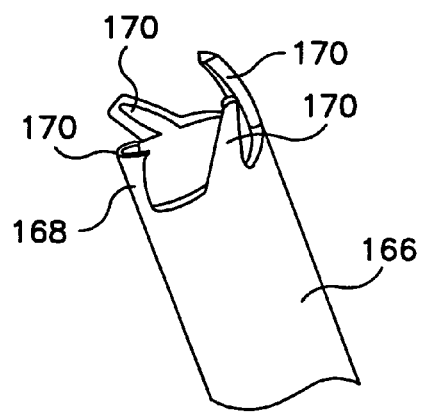
FIG. 16 is a perspective view of a tubular member having a set of blades extending from a distal end according to the invention.
Figure 17:
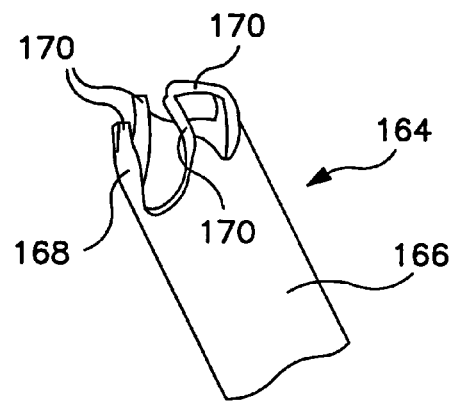
FIG. 17 illustrates the tubular member of FIG. 16 after the blades have been inwardly directed and twisted to be outwardly facing according to the invention.
Figure 18:
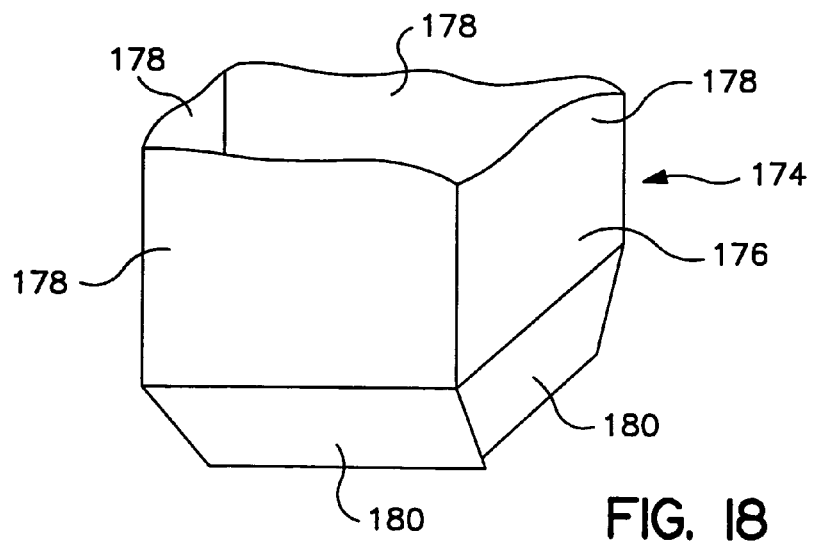
FIG. 18 illustrates an alternative embodiment of a cutting device to form a central opening in a receptacle according to the invention.

Cutting mechanism 100 may be constructed from essentially any type of rigid material onto which a sharpened edge may be formed. Examples of materials that may be employed to construct cutting mechanism 100 include etched or punched hardened stainless steel, syndiotactic polystyrene, other hard plastics, and the like. One convenient way to construct cutting mechanism 100 is by use of a mold into which a liquid metal is placed. For example, as shown in FIG. 15, a set of support members 102 may be formed within a mold by flowing liquid metal through channels 112. Once the support members have been formed, they may be separated from channels 112 and the lades bent downward to the desired angle as previously described.

Figure 9:
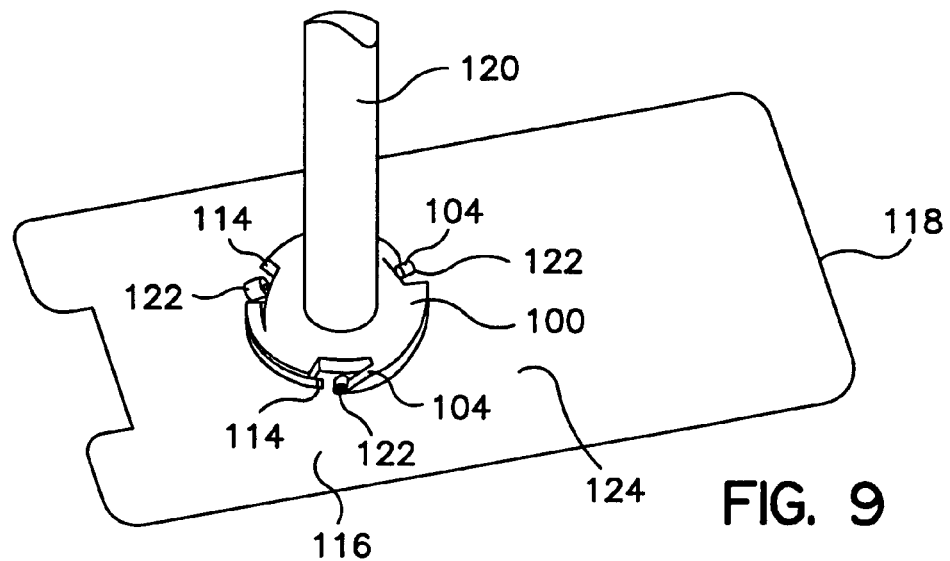
FIG. 9 is a top view of the cutting mechanism of FIG. 6 that is being rotated by a tubular member to form elongate openings in a receptacle according to the invention.
Figure 10:
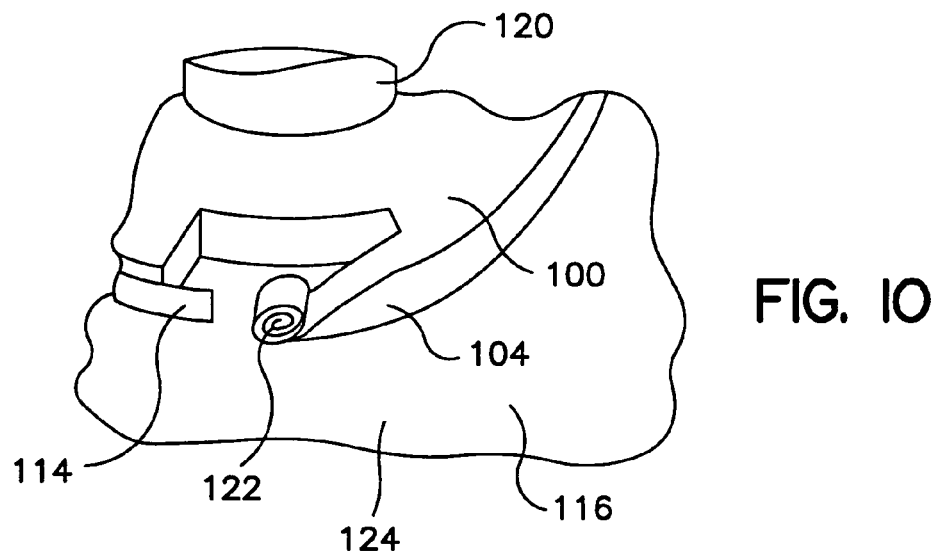
FIG. 10 is a more detailed view of one of the blades of the cutting mechanism of FIG. 9.
Figure 11:
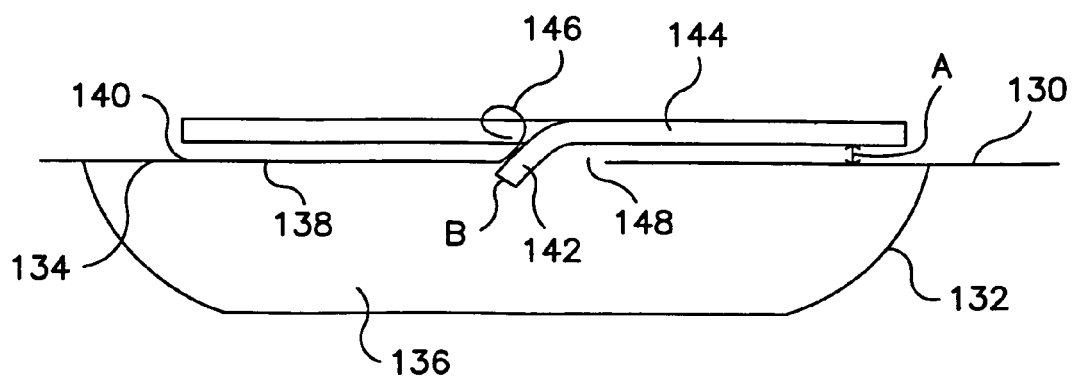
FIG. 11 is a schematic view of a cutting mechanism that is being employed to form an elongate opening in a receptacle.

Referring now to FIG. 9, use of cutting mechanism 100 to form multiple elongate openings 114 in a cover 116 of a receptacle 118 will be described. Receptacle 118 includes a circular cavity (hidden from view) in a manner similar to receptacle 10 of FIG. 1. However, it will be appreciated that the invention is not intended to be limited to the use of cutting mechanism 100 with a specific receptacle. Cutting mechanism 100 is shown coupled to a tubular member 120 that may be rotated to rotate support member 102. Conveniently, tubular member 120 may be employed to extract the powder from the cavity after openings 114 are formed. Optionally, tubular member 120 may include blades at a distal end for simultaneously forming an outlet opening in receptacle 118. However, tubular member 120 may also be used without blades, e.g., when the outlet opening is separately formed.

To form openings 114, support member 102 is moved vertically downward until blades 104 pierce cover 116 and enter into the cavity. Support member 102 is then rotated through an angle to cut portions 122 of cover 116. As support member 102 is rotated, cut portions 122 curl on top of an exterior surface 124 of cover 116. In this way, the cut material is forced outside of the cavity so as to not interfere with air flow through the cavity when extracting the powder.

Figure 12:
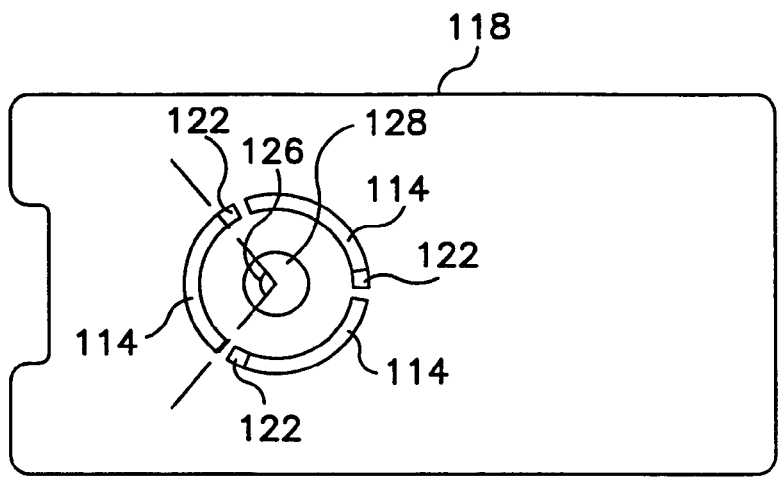
FIG. 12 is a top plan view of the receptacle of FIG. 9 showing the elongate openings that have been form by the cutting mechanism, and also showing a central outlet opening.
Figure 13:
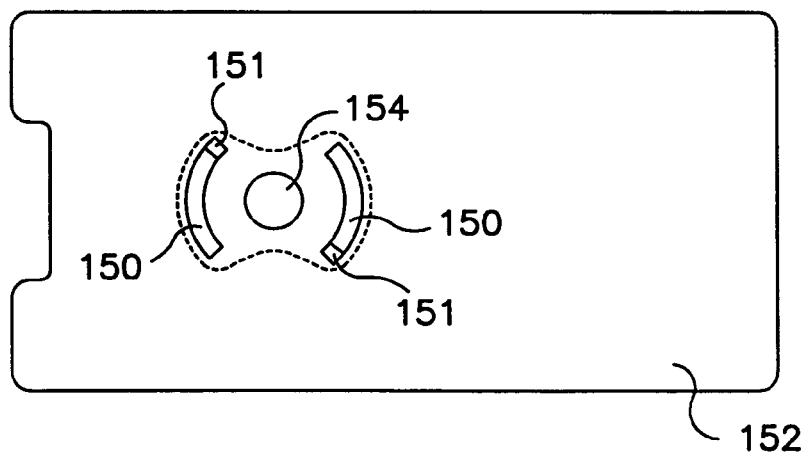
FIG. 13 illustrates an alternative embodiment of a receptacle having a pair of curved outer openings and a central opening according to the invention.
Figure 14:
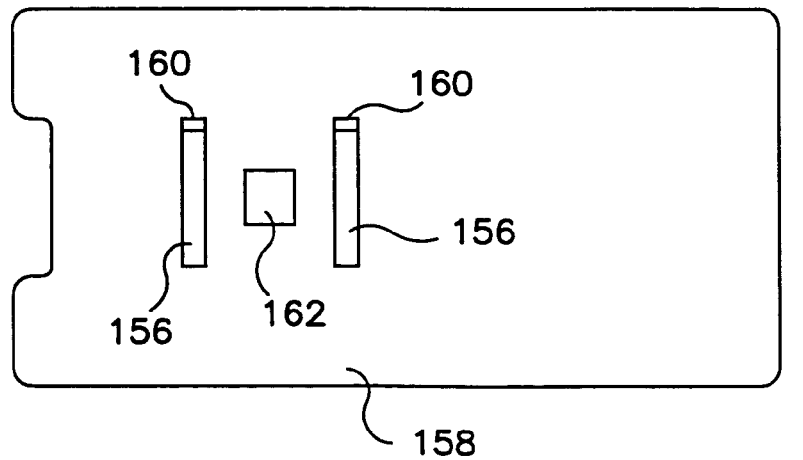
FIG. 14 illustrates still another embodiment of a receptacle having a pair of parallel outer openings and a central opening according to the invention.

FIG. 12 illustrates receptacle 118 after openings 114 have been formed. As shown, openings 114 are curved in geometry and together form a circle of inlet openings 114. Such a configuration is particularly advantageous when receptacle 118 includes a cavity with a generally circular outer periphery. In this way, openings 114 are formed adjacent the outer periphery of the cavity. As such, when air or other gases are drawn into the cavity, they will flow along the outer periphery of the cavity to assist in removing the powder as described generally in co-pending U.S. Application Ser. No. 60/172,317, previously incorporated by reference.

As further shown in FIG. 12, each of openings 114 is formed at an angle 126 that is within the range from about 70 degrees to about 115 degrees. As previously described, this angle range may be varied depending on the desired size of outlet openings 114 and the number of blades included in cutting mechanism 100.

Also shown in FIG. 12 is a central outlet opening 128. As previously described, this opening may conveniently be formed with tubular member 120 while openings 114 are being formed or, alternatively, may be separately formed. After openings 114 and 126 have been formed, powder may be extracted from the receptacle by flowing a gas through inlet openings 114, through the cavity and out outlet opening 128. The size of openings 114 and 128 may be configured to accelerate the flow of air through the cavity of the receptacle as described in co-pending application Ser. No. 60/172,317, previously incorporated by reference.

In some cases, it may be desirable to form inlet openings 114 and/or outlet opening 128 while receptacle 118 is within an aerosolizing apparatus. In this way, the openings do not need to be preformed prior to insertion of the receptacle into the aerosolizing apparatus. Accordingly, in one aspect of the invention the powder may be extracted from receptacle 118 while cutting mechanism 100 remains engaged with the receptacle as illustrated in FIG. 9. In such a case, a gas stream is flowed through at least a portion of tubular member 120 to cause air or other gases to be drawn through inlet openings 114, through the cavity and out tubular member 120. Conveniently, a gas may be flowed through at least a portion of feed tube 120 using any of the apparatus of the previously referenced patents and patent applications.

In a further aspect, the openings between blades 104 may be configured to be offset from inlet openings 114 of the receptacle prior to aerosolization. In this way, when a gas is flowed through tubular member 120, air is drawn tangentially into the cavity to create a vortex within the cavity. The vortex assists in scrubbing the receptacle walls to remove any adhered powder.

One convenient way for forming inlet openings in a receptacle and then extracting the powder is illustrated schematically in FIG. 11. In FIG. 11 a receptacle 130 is shown which may be similar to receptacle 118 as previously described. Receptacle 132 comprises a receptacle body 132 having a cover 134 which encloses a cavity 136 containing the powder. Cover 134 includes an exterior surface 140 and an interior surface 138. As an outer blade 142 of a cutting mechanism 144 is moved through cover 134, a cut portion 146 is forced upward and out of cavity 136. As outer blade 142 is further moved through cover 134, cut portion 146 curls about itself on top of exterior surface 140 in a manner similar to that previously described in connection with FIG. 9. During cutting and powder extraction, cutting mechanism 144 may conveniently be spaced apart from cover 134 by a distance A. Further, blade 142 may have a width, B (shown extending into the page of FIG. 11), to form an opening 148 having approximately the same width. The relation between the spaced apart distance A and the width B may be such that A equals B or A is greater than B. In such cases, a sufficient flow of gases into opening 148 may be provided so that cutting mechanism 144 may be maintained in place during the powder extraction process in a manner similar to that previously described.

Cutting mechanism 100 may be modified to accommodate other types of receptacles having different cavity shapes. For example, as shown in FIG. 13, the cutting mechanism may be modified so that a pair of curved openings 150 are formed in a receptacle 152. As openings 150 are formed, cut portions 151 of the cover curl on top of the cover. Conveniently, receptacle 152 may be configured to have a cavity similar to that previously described in connection with FIG. 4. Optionally, the cutting mechanism may include a center cutting device to form a central opening 154 in a manner similar to that described in connection with receptacle 118 of FIG. 12.

In some cases, the cutting mechanism may be configured to be moved through a cover in a non-rotational manner. For example, as illustrated in FIG. 14, a pair of parallel openings 156 may be formed by translating the blades through the cover of a receptacle 158. In so doing, cut portions 160 are curled on top of the cover in a manner similar to that previously described. Receptacle 158 also includes a central opening 162. Optionally, central opening 162 may be formed with a separate hole forming mechanism as described hereinafter.

Referring now to FIGS. 16 and 17, a process will be described for producing a central opening in a receptacle using a hole forming device 164. Merely by way of example, hole forming device 164 may be employed to produce central openings 128, 154, or 162 of the receptacles of FIGS. 12, 13, and 14, respectively. Hole forming device 164 may be configured to be a stand alone device or may be incorporated into a rotatable cutting mechanism, such as cutting mechanism 100 as previously described. For example, hole forming device 164 may extend through opening 108 of cutting mechanism 100 to form a central opening at the same time outer openings are formed. Hole forming device 164 comprises a tubular member 166 having a distal end 168. Formed at distal end 168 are a plurality of blades 170, with four being shown for convenience of illustration. However, it will be appreciated that other numbers of blades may be provided at distal end 168. As shown in FIG. 16, blades 170 have been formed by simply machining material from distal end 168. As shown in FIG. 17, blades 170 are then pushed inward and then rotated 90 degrees to form a plurality of inwardly and outwardly facing blades. Alternatively, blades 170 may be configured using a molding process, or may be created from a single sheet prior to rolling the sheet into a tube.

To form an opening in a receptacle, tubular member 166 is moved downward until blades 170 pierce the cover. Tubular member 166 is then rotated to move the blades 170 through the cover.

One particular advantage of hole forming device 164 is that it may remain extending into the cavity after the central opening has been formed. In this way, as gases flow through the inlet openings and through the cavity, they will pass upwardly into tubular member 166 along with the extracted powder. The powder that is entrained in the gas stream will then pass through tubular member 166 and into a capture chamber, mouthpiece, or other device where it will be available for inhalation by a patient. The particular configuration of blades 170 is advantageous in that they permit the cover to be opened while still permitting sufficient gas flow through tubular member 166 to permit the powder to be extracted and aerosolized. In a preferred embodiment, hole forming device 164 is rotated through an angle such that the openings between blades 170 are coincident with openings between cut flaps in the receptacle cover.

Referring now to FIG. 18, another embodiment of a hole forming device 174 will be described. Hole forming device 174 comprises a tubular member 176 that is formed of four perpendicular walls 178. Extending from walls 178 are a set of blades 180 that angle inwardly similar to a half opened box. As blades 180 are forced downward into a cover, a generally square or rectangular hole is formed. One particular advantage of hole forming device 174 is that it may be operated in a manner similar to a punch so that no rotation is needed in order to form a hole. Further, the orthogonal nature of walls 178 tends to mate with the square or rectangular hole that is formed, thereby providing a seal between tubular member 176 and the cover of the receptacle.

Figure 19:
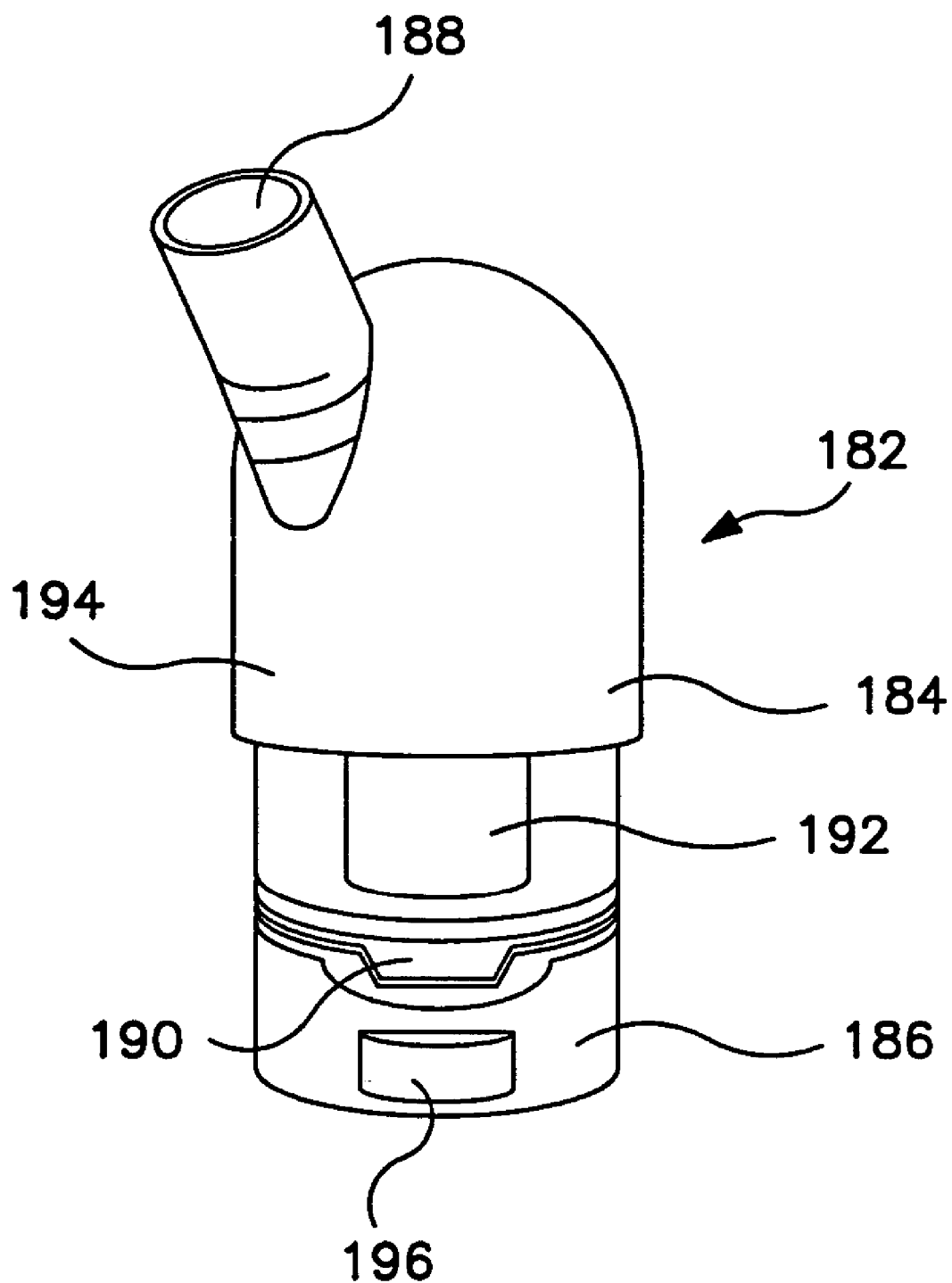
FIG. 19 is a schematic diagram of one embodiment of an aerosolizing device according to the invention.

Referring now to FIG. 19, one embodiment of an aerosolizing apparatus 182 will be described. Apparatus 182 comprises a housing 184 having a base 186 and a mouthpiece 188. Included within base 186 is an opening 190 for receiving a receptacle, including any of the receptacles described herein. Held within base 186 is a tubular member 192 that leads to a capture chamber (hidden from view) that is in communication with mouthpiece 188. Coupled to tubular member 192 is a cutting mechanism (hidden from view) for forming inlet openings in the receptacle, and may be similar to any of the cutting mechanisms described herein. Further, tubular member 192 may include blades at a distal end (hidden from view) in a manner similar to the other embodiments described herein. In this way, a receptacle may be placed into opening 190, and housing 184 compressed to force the various blades into the cover of the receptacle in a manner similar to that previously described. Base 186 may then be rotated relative to a top section 194 of housing 184 to move the various blades through the cover in a manner similar to the other embodiments described herein. Once the openings have been formed, a button 196 may be operated to release an amount of pressurized gas to draw air through the inlet openings of the receptacle, through the cavity of the receptacle, and out the outlet opening in a manner similar to that described with previous embodiments. The gas and entrained powder exiting the receptacle flow through tubular member 192 and are received into the capture chamber. The patient may then inhale from mouthpiece 188 to extract the powder. Conveniently, the released gas may be flowed through a portion of tubular member 192 in a manner similar to that described in connection with the apparatus that have been described in the documents previously incorporated herein by reference to extract the powder from the receptacle. Optionally, apparatus 182 may be a breath actuated device where the patient inhales from mouthpiece 188 to cause the gas stream to flow through tubular member 192 in order to extract the powder from the receptacle.

During the powder extraction process, the blades of the cutting mechanism may be maintained within the cavity. In such an event, the cutting mechanism may have a support member that is spaced above the cover of the receptacle by a distance defined in terms of the width of the inlet openings in a manner similar to that previously described. In this way, the number of steps that need to be performed by the operator may be kept to a minimum, thereby greatly simplifying its operation.

The invention has now been described in detail for purposes of clarity of understanding. However, it will be appreciated that certain changes and modifications may be practiced within the scope of the appended claims.

What is claimed is:

1. A method for forming multiple openings in a receptacle, the method comprising:
   providing a receptacle having a cover with an exterior surface and an interior surface covering a cavity;
   providing a cutting mechanism having multiple blades;
   piercing the cover with the blades by moving the cutting mechanism in a forward direction; and
   moving the blades in a direction other than the forward direction through the cover to create multiple elongate openings in the cover and thereby provide access into the cavity, with the cut portion being removed onto the exterior surface and away from the cavity as the openings are created.

2. A method as in claim 1, wherein moving the blades in a direction other than the forward direction comprises rotating the cutting mechanism after the piercing step.

3. A method as in claim 2, wherein a cut portion curls upon rotation of the cutting mechanism.

4. A method as in claim 2, wherein multiple elongate openings are formed simultaneously when the cutting mechanism is rotated.

5. A method as in claim 4, wherein the number of blades is three, and further comprising rotating the cutting mechanism through an angle in the range from about 70 degrees to about 115 degrees.

6. A method as in claim 1, wherein the cutting mechanism further comprises a support member, and wherein the blades are angled in a forward direction relative to the support member by an angle in the range from about 50 degrees to about 80 degrees, and further comprising moving the blades through the cover in the forward direction such that the angled blades facilitate outward curling of the cut portions of the receptacle cover.

7. A method as in claim 6, wherein the blades are angled in a forward direction relative to the support member by an angle in the range from about 60 degrees to about 70 degrees.

8. A method as in claim 1, wherein the cavity has an outer periphery, and further comprising forming an opening near the outer periphery.

9. A method as in claim 8, wherein at least a portion of the outer periphery is curved, and wherein moving the blades comprises rotating the cutting mechanism such that the opening near the outer periphery is curved along the outer periphery.

10. A method as in claim 1, wherein the cutting mechanism further includes a center cutting device, and further comprising forming a central opening in the cover with the center cutting device.

11. A method as in claim 10, wherein the center cutting device comprises a tubular member extending from a support member, and wherein the step of forming the central opening comprises piercing the cover with the center cutting device and then rotating the support member.

12. A method for aerosolizing a powder, the method comprising:
   providing a receptacle having a cover with an exterior surface and an interior surface covering a cavity that contains a powder;
   providing a cutting mechanism having at least one outer blade and a plurality of inner blades;
   piercing the cover with the outer blade and the inner blades by moving the blades in a forward direction;
   moving the outer blade in a direction other than the forward direction through the cover to cut a portion of the cover to create an outer elongate opening in the cover, with the cut portion being removed away from the cavity as the opening is created; and
   drawing air through the outer opening, through the cavity and out the inner opening to extract the powder from the receptacle and to aerosolize the powder.

13. A method as in claim 12, wherein the cutting mechanism further comprises a support member, and further comprising maintaining the support member spaced apart from the cover when cutting the openings and when extracting the powder.

14. A method as in claim 13, wherein the outer opening has a width, B, and further comprising maintaining the support member spaced apart from the cover by a distance, A, where A is greater than or equal to B.

15. A method as in claim 14, wherein the width, B, is in the range from about 0.3 mm to about 2 mm.

16. A method as in claim 13, wherein the cutting mechanism further comprises a tubular member extending from a support member, wherein the inner blades are on the tubular member, and further comprising rotating the support member to create the outer and the inner openings.

17. A method as in claim 16, wherein the drawing step comprises flowing a gas stream through at least a portion of the tubular member.

18. A method as in claim 12, wherein the cutting mechanism comprises a support member, wherein the blade is angled in a forward direction relative to the support member by an angle in the range from about 50 degrees to about 80 degrees, and wherein moving the blades comprises rotating the support member such that the blade is moved through the cover in the forward direction.

19. A method as in claim 18, wherein the cutting mechanism includes multiple blades such that multiple elongate openings are formed simultaneously about the inner opening when the cutting mechanism is rotated.

20. A method as in claim 12, wherein the cavity has an outer periphery, and further comprising forming the outer opening near the outer periphery.

21. An aerosolizing apparatus comprising:
a housing that is adapted to receive a receptacle having a cover with an exterior surface and an interior surface covering a cavity that contains a powder;
a hole forming device disposed within the housing, wherein the hole forming device is adapted to form at least one inlet opening and an outlet opening in the cover;
an aerosolizing system that is adapted to extract the powder from the receptacle by drawing air through the inlet opening, through the receptacle and out the outlet opening;
wherein the hole forming device comprises a movable support member capable of being moved through the cover in a forward direction, the movable member having at least one outer blade extending in the same forward direction from the support member at an angle in the range from about 50 degrees to about 80 degrees and at least one inner blade, and a moving mechanism to move the support member in a direction other than the forward direction to move the outer blade through the cover and cause a cut portion of the cover to be removed away from the cavity to form the at least one inlet opening, and to cut an outlet opening with the inner blade.

22. An apparatus as in claim 21, wherein the hole forming device further comprises a plurality of the outer blades, and a tubular member extending downward from the support member, the tubular member being surrounded by the outer blades, and the tubular member having a distal end that includes a plurality of inwardly and outwardly facing blades.

23. An apparatus as in claim 22, wherein the outer blades have a width in the range from about 0.3 mm to about 2 mm.

24. An apparatus as in claim 22, further comprising a gas source that is configured to flow a gas stream through at least a portion of the tubular member to draw gases through the inlet openings, through the cavity and through the tubular member.

25. An apparatus as in claim 22, further comprising a mouthpiece, wherein suction on the mouthpiece causes a gas stream to flow through at least a portion of the tubular member to draw gases through the inlet openings, through the cavity and through the tubular member.

26. An aerosolizing system comprising:
at least one receptacle comprising a receptacle body having a cover with an exterior surface and an interior surface covering a cavity that contains a powder;
an aerosolizing apparatus comprising a housing that is adapted to receive the receptacle;
a hole forming device disposed within the housing, wherein the hole forming device is adapted to form at least one inlet opening and an outlet opening in the cover; and
a gas flow system that is adapted to extract the powder from the receptacle by drawing air through the inlet opening, through the receptacle and out the outlet opening;
wherein the hole forming device comprises a movable support member capable of being moved through the cover in a forward direction, the movable member having at least one outer blade extending in the same forward direction from the support member at an angle in the range from about 50 degrees to about 80 degrees and at least one inner blade, and a moving mechanism to move the support member in a direction other than the forward direction to move the outer blade through the cover and cause a cut portion of the cover to be removed away from the cavity to form the at least one inlet opening, and to cut an outlet opening with the inner blade.

27. A system as in claim 26, wherein the cavity has a circular outer periphery, and further comprising a plurality of outer blades that are arranged to form a plurality of inlet openings about the outer periphery to surround the outlet opening.

28. A system as in claim 27, wherein the hole forming device further comprises a tubular member extending downward from the support member, the tubular member being surrounded by the outer blades, and the member having a distal end that includes a plurality of inwardly and outwardly facing blades.

29. An apparatus as in claim 28, further comprising a gas source that is configured to flow a gas stream through at least a portion of the tubular member to draw gases through the inlet openings, through the cavity and through the tubular member.

30. An apparatus as in claim 28, further comprising a mouthpiece, wherein suction on the mouthpiece causes a gas stream to flow through at least a portion of the tubular member to draw gases through the inlet openings, through the cavity and through the tubular member.

* * * * *